United States Patent [19]

Kim

[11] Patent Number: 5,004,738
[45] Date of Patent: Apr. 2, 1991

[54] 1,1-DIOXOPENICILLANOYL OXYMETHYL D-6-(α-(METHYLENEAMINO) PHENYLACETAMIDO)-PENICILLANATE AND A PROCESS FOR THE PREPARATION THEREOF

[76] Inventor: Young Sul Kim, Cosmos Mansion 1002, #302-62 Ichon-Dong, Yongsan-Ku, Seoul, Rep. of Korea

[21] Appl. No.: 383,435

[22] Filed: Jul. 24, 1989

[30] Foreign Application Priority Data

Jun. 20, 1989 [KR] Rep. of Korea ............... 89-8501

[51] Int. Cl.$^5$ .............. A61K 31/43; C07D 499/08; C07D 499/32
[52] U.S. Cl. .............................. 514/195; 540/306; 540/318; 540/331
[58] Field of Search .............. 540/306, 318, 331; 514/195

[56] References Cited

U.S. PATENT DOCUMENTS

| | | | |
|---|---|---|---|
| 4,342,772 | 8/1982 | Godtfredsen et al. | 514/195 |
| 4,377,590 | 3/1983 | Myers | 514/195 |
| 4,393,001 | 7/1983 | Jasys | 540/306 |
| 4,432,987 | 2/1984 | Barth et al. | 514/195 |
| 4,503,040 | 3/1985 | Barth | 514/196 |

FOREIGN PATENT DOCUMENTS 1081093 8/1967 United Kingdom.

OTHER PUBLICATIONS

Fu et al., *Antimicrobial Agents and Chemotherapy*, vol. 15, No. 2, 171–176 (1979).
Greenwood et al., *J. Antimicrobial Chemotherapy*, vol. 10, 117–123 (1982).

*Primary Examiner*—Jose G. Dees
*Assistant Examiner*—Vera C. Clarke
*Attorney, Agent, or Firm*—Birch, Stewart, Kolasch & Birch

[57] ABSTRACT

A pharmaceutical compound which comprises reacting the sodium penicillanic acid 1,1-dioxides with chloroiodomethane in the presence of a solvent to produce chloromethylpenicillanate 1,1-dioxides, reacting the chloromethylpenicillanate 1,1-dioxides with a sodium iodide to produce iodomethylpenicillanate 1,1-dioxides, and reacting the iodomethylpenicillanate 1,1-dioxide with sodium methampicillin and is effective in the treatment of bacterial infections in a mammal.

8 Claims, No Drawings

1,1-DIOXOPENICILLANOYL OXYMETHYL D-6-(α-(METHYLENEAMINO) PHENYLACETAMIDO)-PENICILLANATE AND A PROCESS FOR THE PREPARATION THEREOF

BACKGROUND OF THE INVENTION

1. Field of the Invention

The present invention relates to beta-lactamase inhibitors for medical use which are hydrolyzable in vivo and a process for the preparation thereof. More particularly, the present invention relates to 1,1-dioxopenicillanoyl oxymethyl D-6-[α-(methyleneamino) phenylacetamido]-penicillanate or pharmaceutically acceptable salts thereof represented by the following formula (I) and (I'):

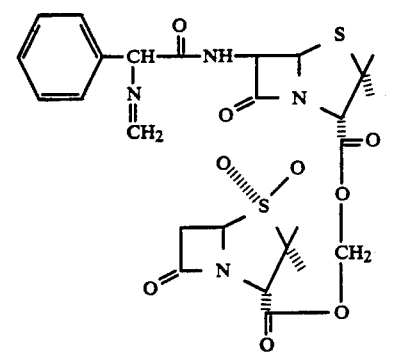

(I)

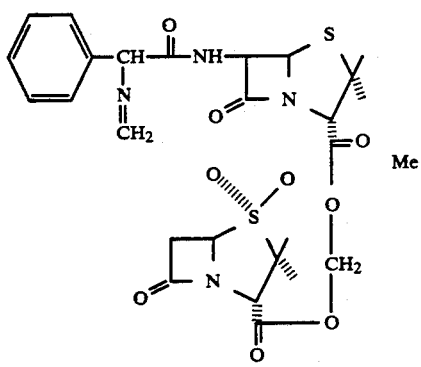

(I')

wherein Me is hydrochloride, sulfuric acid, phosphoric acid, maleic acid, succinic acid, methanesulfonic acid, or p-toluenesulfonic acid.

2. Description of the Prior Art

Sulbactam (penicillanic acid 1,1-dioxide) or pharmaceutically acceptable salts thereof are well known in the art as a kind of β-lactamase-resistance antibiotic. Although sulbactam or pharmaceutically acceptable salts thereof alone are a poor inhibitor of β-lactamases, when sulbactam or pharmaceutically acceptable salts thereof are reacted with β-lactamase inhibiting antibiotics, the compounds exhibit a modest increase in inhibition of the enzymatic hydrolysis of antibiotics [FU, K.P. and NEU, H.C., Comparative Inhibition of β-lactamase by novel β-lactam compounds. *Antimicrobial Agents and Chemotherapy* 15, No.2, 171–176 (1979)].

Methanpicillin and its salts are disclosed in U.K. Patent No. 1,081,093, Korean Patent Publication 82-740 issued to the present inventor, and Belgium Patent 867,859 and have a marked increase in inhibition against gram-positive and gram-negative bacteria.

6-(aminoacyloxymethyl) penicillanic acid 1,1-dioxides as β-lactamose inhibitors are disclosed in U.S. Pat. No. 4,503,040. While the compounds are effective in enhancing the activity of β-lactam antibiotics in general, their preferred use is found in their combination with a penicillin or cephalosporin of established clinical utility, viz., amoxicillin, ampicillin, apalacillin, azlocillin, azthreonam, bacampicillin, carbenicillin, carbenicillin indanyl, carbenicillin phenyl, cefaclor, cefadroxil, cefaloram, cefamandole, cefamandole nafate, cefaparole, cefatrizine, cefazolin, cefmenoxime, cefonicid, cefodizime, cefoperazone, ceforanide, cefotaxime, cefotiam, cefotetan, cefoxitin, cefsulodin, ceftazidime, ceftizoxime, ceftriaxone, cefuroxime, cephacetrile, cephalexin, cephaloglycin, cephaloridine, cephalothin, cephapirin, cephradine, cyclacillin, epicillin, furazlucillin, hetacillin, levopropylcillin, mecillinam, mezlocillin, penicillin G, penicillin V, phenethicillin, piperacillin, pirbenicillin, pivampicillin, sarmoxicillin, sarpicillin, suncillin, talampicillin or ticarcillin, or a pharmaceutically acceptable salt thereof. However, a pharmaceutical compound of sulbactam reacted with methampicillin has never been disclosed in the art and also the marked increase in activity of the compound in treating bacterial infections has never been disclosed.

SUMMARY OF THE INVENTION

Accordingly, it is an object of the present invention to provide an antibacterial compound or pharmaceutically acceptable salts thereof for medical use and a process for the preparation thereof.

Another object of the present invention is to provide a compound which comprises reacting sulbactam or a pharmaceutically acceptable salt thereof with methanpicillin or a pharmaceutically acceptable salt thereof.

A further object of the present invention is to provide a pharmaceutical compound for treating bacterial infections in a mammal.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a pharmaceutical compound which comprises reacting the sodium penicillanic acid 1,1-dioxides with chloroiodomethane in the presence of a solvent to produce chloromethylpenicillanate 1,1-dioxides, reacting the chloromethylpenicillanate 1,1-dioxides with a sodium iodide to produce iodomethylpenicillanate 1,1-dioxides, and reacting the iodomethylpenicillanate 1,1-dioxide with sodium methampicillin. The present compound is effective in the treatment of bacterial infections in a mammal.

DESCRIPTION OF THE PREFERRED EMBODIMENTS

Referring now in detail to the present invention, there is provided an antibacterial compound for medical use which comprises reacting the sulbactam or a pharmaceutically acceptable salt thereof with methampicillin or a pharmaceutically acceptable salt thereof, and a process for the preparation thereof.

Thus the present invention is directed to a pharmaceutical compound which comprises reacting sulbactam, 3.3-dimethyl-7-oxo-4thia-1-azabicyclo(3.2.0)heptane-2-carboxylic acid, 4-4-dioxide [2S(2α,5α)] having the following formula (II):

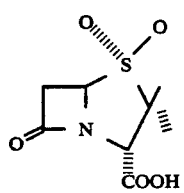
(II)

with methampicillin, 6-[D(-)-α-[(methyleneamino phenylacetamido)]-pencillanic acid having the following formula (III):

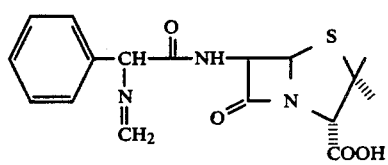
(III)

The reaction scheme of the present invention is as follows:

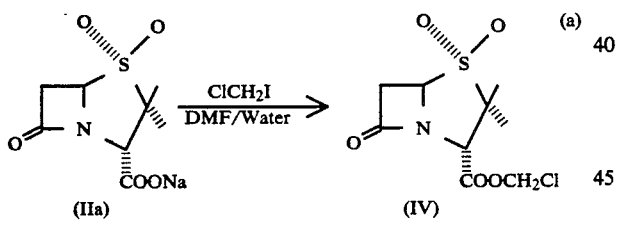
(a)

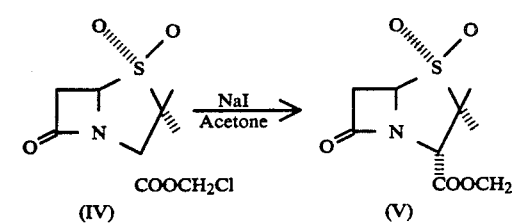
(b)

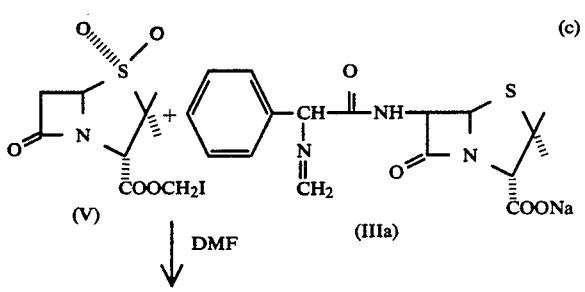

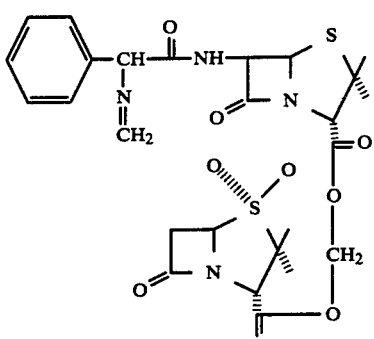
(I)

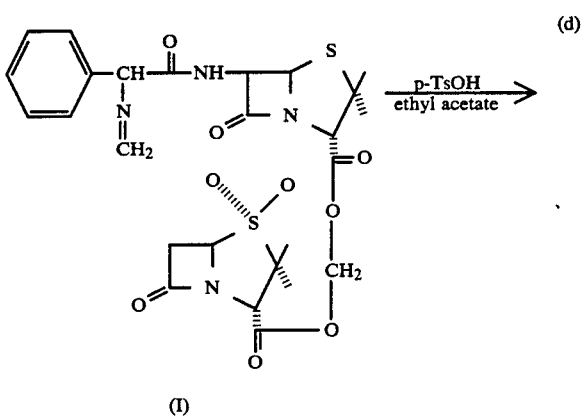
(d)

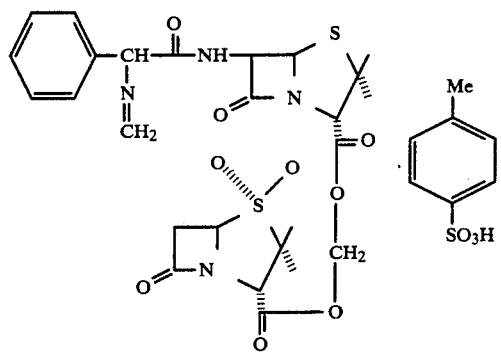
(I')

wherein Me is hydrochloride, sulfuric acid, phosphoric acid, maleic acid, succinic acid, methanesulfonic acid, or p-toluenesulfonic acid.

The process for the preparation of new compound (I) is as follows:

The present invention is to provide a compound (I) which comprises (a) reacting sodium sulbactam (IIa) with chloroiodomethane (ClCH$_2$I) in the presence of a mixture solvent such as a combined dimethylformamide (DMF) and water to produce chloromethylpenicillinate 1,1-dioxides (IV), (b) reacting the produced chloromethylpenicillinate 1,1-dioxides (IV) with sodiumiodide (NaI) in the presence of acetone at room temperature to produce iodomethylpenicillinate 1,1-dioxides (V), and (c) reacting the produced iodomethylpenicillinate 1,1-dioxides (V) with sodium methamicillin (III) in the presence of dimethylformanide (DMF) to produce 1,1- dioxopenicillanoyl oxymethyl D-6-[(α-methyleneamino) phenylacetamido]-penicillanate (I).

Also, referring in detail to step (d), there is illustrated an additional embodiment of a pharmaceutical compound in accordance with the present invention.

The process for making new compound (I') is as follows:

The present invention is to provide a compound (I') which comprises (d) reacting the produced compound (I) with p-toluenesulfonic acid monohydrate in the presence of ethylacetate to produce toluenesulfonic acid 1,1-dioxppenicillanoyl oxymethyl D-6-[(α-methyleneamino) phenylacetamido]-penicillanate (I') in accordance with the present invention.

In step (a), the mixture solvent is combined dimethylformamide with water in a weight ratio about 1:1 to 10:1, preferably in a weight ratio of 5:1.

In step (b), the reaction is conducted for about 10-50 hours, preferably for 20-40 hours.

In step (c), the reaction is conducted at a temperature of about −10°-10° C., preferably −5°-5° C. Also, the crystallization of the compound (I) uses a solvent such as hexane, ethylether, cyclohexane, isopropylether, ethylacetate, or a mixture thereof.

In step (d), an amount of a pharmaceutically acceptable acid is same to molar equivalents of the compound (I) of the present invention. The acid is dissolved in an organic solvent such as ethylacetate. The compound (I') of the present invention is recrystallized by using hexane, cyclohexane, ethylenechloride, isopropylether, etc. at a temperature of about 0°-10° C.

The compounds of the formulae (I) and (I') are useful as inhibitors of beta-lactamase enzymes, by this mechanism, these compounds enhance the activity of beta-lactam antibiotics, particularly against those microorganisms which are resistant or partially resistant to the beta-lactam antibiotic through the production of enzymes (beta-lactamases) which would otherwise destroy or partially destroy the beta-lactam antibiotic. In this matter, the antibacterial spectrum of activity of the beta-lactam antibiotic is expanded.

Also, the compounds of the formulae (I) and (I') are effective as molar equivalents of antibacterials through their in vivo hydrolysis to the corresponding beta-lactamase inhibitors of the formulae (II) and (III) such as sulbactam and methamicillin. It is considered that there is an enhancement of antibacterial effectiveness when the antibacterial activity of a beta-lactamase inhibiting substance and a beta-lactam antibiotic is significantly greater than the sum of the antibacterial activities of the individual components.

Also encompassed by the present invention are antibacterial compounds having the stereochemical formula.

The beta-lactamase inhibiting activity in vivo of the compound is illustrated as follows:

(1) In vitro antibacterial activity test 2 fold dilutions of the testing compounds were employed by using agar dilution method of Mueller Hinton Agar. After 18 hours at 37° C., the susceptibility (MIC) of the test organism was accepted as the lowest concentration of compound capable of producing complete inhibition of growth as judged by the naked eye. MIC value for compounds (I) or (I') against several microorganisms are shown in Table I.

TABLE I

| In vitro antibacterial activity of compounds (I) or (I') | |
|---|---|
| Microorganism | MIC (mcg/ml) |
| Streptococcus faecium MD8 | 0.781 |
| Staphylococcus aureus SG511 | 0.098 |
| Escherichia coli DC2 | 1.563 |
| Enterobacter cloacae 132E | 1.563 |

(2) Toxic symptoms test

The animals used in this test were male ICR mice weighing about 25 g with about 4-5 weeks old. 1-2 days prior to test ignition, the testing compound dissolved in olive oil were orally administrated and the animals were observed that $LD_{50}$ (mg/kg) > 10,000 mice. No toxic symptoms were noted in any of the dosed animals.

The present invention will now be described in more detail in connection with the following examples which should be considered as being exemplary and not limiting the present invention.

EXAMPLE 1

The method of preparation of chloromethylpenicillanate 1,1-dioxide 4.0 g of sodium penicillanic acid 1,1-dioxide is dissolved in 90 ml of dimethylformamide and 7 ml of water and is stirred at room temperature. 25 g of chloroidomethanol is added the solution and then the solution is stirred at room temperature for 64 hours. After the reaction is completed, 80 ml of methylenechloride is added separately to the solution and then is separated organic layer from the solution. The resulting solution is washed three times with 20 ml of brine water and dried with magnesium sulfate ($MgSO_4$). The treated solution is filtered and evaporated in vacuo of the solvent to dryness. Finally, 3.5 g of chloromethylpenicillanate 1,1-dioxide is obtained by column chromatography with a mixture solvent of hexane and methylacetate (2:1).

$^1H$ NMR($CDCl_3$) ppm 6:1.5(s,3H), 1.7(s,3H), 3.55(d,2H)
4.5(s,1H), 4.7(t,1H), 5.7(d,1H), 6.0(d,2H)

EXAMPLE 2

The method of preparation of 1,1-dioxopenicillanoyl oxymethyl-D-6-[α-(methyleneamino) phenylacetamido]-penicillanate.

12.0 g of iodomethylpenicillanate 1,1-dioxide is dissolved in dimethylformamide and 1.4.0 g of sodium methamicillin is added to the solution and is stirred in ice water for 6 hours. After the reaction is completed, 400 ml of ethylacetate and 300 ml of water are added to the resulting solution and then the produced organic layer is separated therefrom. The separated solution is washed three times with water and brine water, dried with magnesium sulfate, filtered, and evaporated in vacuo of the solution to dryness. Finally, 14.4 g of 1,1-dioxopenicillanoyloxymethyl-D-6-[α-(methyleneamino) phenylacetamido]-penicillanate is obtained by column chromatography with a mixture solution of hexane and ethylacetate (2:1).

m.p: 156°-157° C.

$^1H$ NMR($CDCl_3$)ppm:1.5(s,3H) 1.6(s,6H), 1.7(s,3H), 3.5(d,2H), 4.3-4.6(m,4H), 5.6(bs,2H), 5.9(s,2H), 7.3(s,5H), 7.4-7.5(bs,2H)

EXAMPLE 3

The method of the preparation of P-toluenesulfonic acid salt 1,1-dioxopenicillanoyloxymethyl D-6-[α-methyleneamino) phenylacetamido]-penicillanate 1.0 g of 1,1-dioxopenicillanoyloxymethyl-D-6-[α-(methyleneamino) phenylacetamido]-penicillanate produced by Example 2 is dissolved in 13 ml of ethylacetate. A mixture solution produced by mixing 325 mg of p-toluenesulfonic acid H$_2$O and 5 ml ethylacetate is added the solution at 0° C. for 20 minutes. Thereafter, the solution is stirred at 0°-10° C. for 2 hours and stirred continuously at room temperature for 1 hour. 8 ml of ethylacetate is added the resulting solution and then the solution is distilled at reduced pressure. The solution is crystallized with isopropylether and filtered to give 1.1 g of p-toluenesulfonic acid 1,1-dioxopenicillanoyloxymethyl D-6-[α-(methyleneamino) phenylacetamido]-penicillanate.

m.p.: 145°-163° C. (decomposition) $^1$H NMR(CDCl$_3$)ppm:1.5(s,3H), 1.6(s,6H), 1.7(s,3H), 2.3(s,3H), 3.5(d,2H), 4.2-4.6(m,4H), 5.2-5.6(br-4H), 7.1-7.6(m,9H), 8.3(br,2H)

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A pharmaceutical compound of 1,1-dioxopenicillanoyl oxymethyl-D-6-[α-(methyleneamino) phenylacetamido]-penicillanate or pharmaceutically acceptable salt thereof represented by the following formulas (I) and (I'):

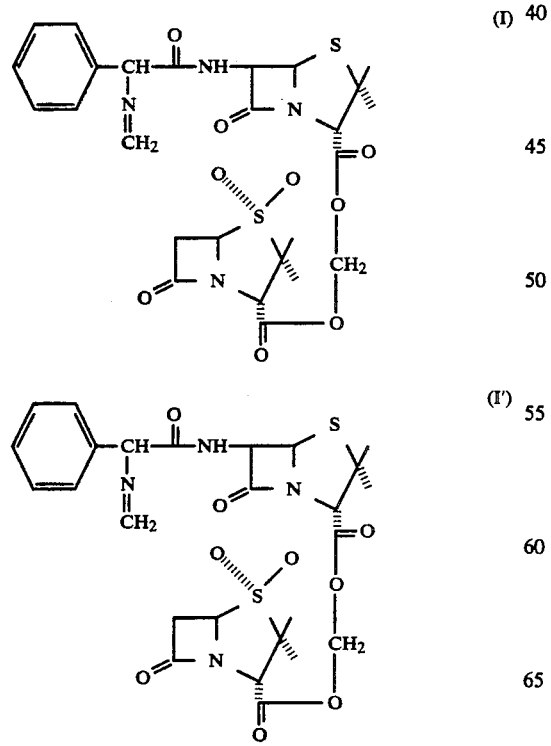

wherein Me is hydrochloride, sulfuric acid, phosphoric acid, maleic acid, succinic acid, methanesulfonic acid, or p-toluenesulfonic acid.

2. A process of the preparation of 1,1-dioxopenicillanoyl oxymethyl-D-6-[α-(methyleneamino) phenylacetamido]-penicillanate which comprises the steps of:
   (a) reacting sodium sulbactam (IIa) with chloroiodomethane (ClCH$_2$I) in a presence of a mixture solvent to produce chloromethylpenicillanate 1,1-dioxide (IV),
   (b) reacting said chloromethylpenicillanate 1,1-dioxide with sodiumiodide (NaI) in presence of a solvent to produce iodomethylpenicillamate 1,1-dioxide (V), and
   (c) reacting said iodomethylpenicillanate 1,1-dioxide (V) with sodium methanicillin (IIIa) in the presence of a solvent to produce said 1,1-dioxopenicillanoyl oxymethyl-D-6-[α-(methyleneamino) phenylacetamido]-penicillanate

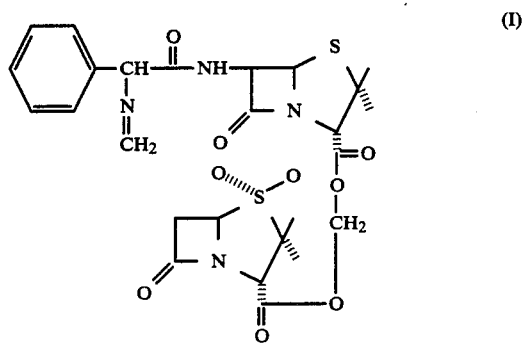

(I)

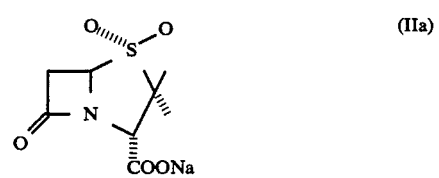

(IIa)

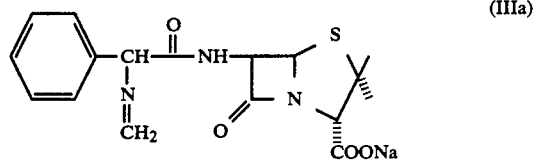

(IIIa)

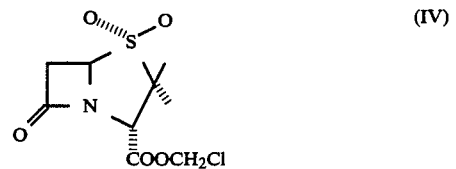

(IV)

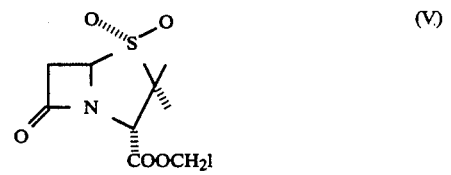

(V)

3. The process of claim 2, wherein in step (a), the mixture solvent is a combined dimethylformamide and water.

4. The process of claim 2, wherein in step (b), the solvent is acetone.

5. The process of claim 2, wherein in step (c), the solvent is dimethylformamide.

6. The method for treating a bacterial infection in a mammal in need thereof which comprises administrating orally to said mammal an antibacterially effective amount of the pharmaceutical compound of claim 1.

7. An antibacterial composition comprising an effective amount of the compound of claim 1 and pharmaceutically acceptable diluent.

8. An antibacterial composition comprising an effective amount of the compound of claim 1 and pharmaceutically acceptable carrier.

* * * * *